(12) United States Patent
Ghose et al.

(10) Patent No.: US 7,101,982 B2
(45) Date of Patent: Sep. 5, 2006

(54) CONTROL OF PH TRANSITIONS DURING CHROMATOGRAPHY

(75) Inventors: Sanchayita Ghose, Newcastle, WA (US); Thomas M. McNerney, Sammamish, WA (US)

(73) Assignee: Immunex Corporation, Seattle, WA (US)

( * ) Notice: Subject to any disclaimer, the term of this patent is extended or adjusted under 35 U.S.C. 154(b) by 172 days.

(21) Appl. No.: 10/112,416

(22) Filed: Mar. 29, 2002

(65) Prior Publication Data

US 2003/0004094 A1 Jan. 2, 2003

Related U.S. Application Data

(60) Provisional application No. 60/280,729, filed on Mar. 30, 2001.

(51) Int. Cl.
*C07K 14/00* (2006.01)

(52) U.S. Cl. .......................... 530/412; 530/350; 514/2; 435/69.1

(58) Field of Classification Search ................ 435/69.1; 514/2; 530/412, 350
See application file for complete search history.

(56) References Cited

U.S. PATENT DOCUMENTS 5,767,064 A * 6/1998 Sims et al. .................... 514/2
6,162,629 A * 12/2000 Baker et al. ................ 435/212

FOREIGN PATENT DOCUMENTS

WO  WO 90/12803  11/1990

OTHER PUBLICATIONS

Clayton and Bushuk, "Ion Exchange Chromatography of Proteins Artifact Separations Resulting From Inadequate pH Control,"*J Chromatog* 21:67–74, 1966.
Frey et al., "Numerical Studies of Multicomponent Chromatography Using pH Gradients," *AIChE Journal* 41(5):171–1183, 1995.
Fuchs et al., "Determination of Optimal Non–Denaturing Elution Conditions From Affinity Columns by a Solid–Phase Screen," *BioTechniques* 31(3):584–596, 2001.
Ghose, "Practical Aspects of Large–Scale Chromatography of Biologicals –Short Course," *International Business Communications,* Nov. 15, 2000.
Jansen et al., "Effect of pH and Concentration on Column Dynamics of Weak Electrolyte Ion Exchange," *AIChE Journal* 42(7):1925–1937, 1996.

* cited by examiner

*Primary Examiner*—Christopher Tate
*Assistant Examiner*—Roy Teller
(74) *Attorney, Agent, or Firm*—Kathleen Fowler

(57) ABSTRACT

The invention provides methods of controlling pH variations during chromatography. In particular embodiments, the invention includes equilibrating and eluting proteins from chromatography resins have a solid phase that possesses a charged functional group on its backbone under controlled conditions of osmolarity and pH. The invention is particularly useful in the purification of proteins that are sensitive to pH transitions such as, for example, the IL-1 Receptor type II protein.

11 Claims, 5 Drawing Sheets

$$K_{Na,H} = \frac{[Na_M^+][H_S^+]}{[H_M^+][Na_S^+]}$$

US 7,101,982 B2

CONTROL OF PH TRANSITIONS DURING CHROMATOGRAPHY

CROSS REFERENCE TO RELATED APPLICATION

This application claims the benefit of provisional U.S. application No. 60/280,729, filed Mar. 30, 2001, the entire disclosure of which is incorporated by reference herein.

FIELD OF THE INVENTION

The invention is in the field of purification of proteins, particularly recombinant proteins, through chromatography.

BACKGROUND

The development of efficient bioseparation processes for the production of high-purity biopharmaceutical products is one of the most pressing process development challenges facing the pharmaceutical and biotechnology industries today. Chromatography, by virtue of its high resolving power has made itself indispensable in downstream purification of biomolecules.

The last decade has seen a plethora of new stationary phase materials with a variety of base-matrix properties, linker arm chemistries and functional groups even for the same mode of chromatographic interaction. These chromatographic media differ in a variety of properties that are relevant to process applications such as capacities (dynamic, static and ionic), resolution, plate height, pressure drop, compressibility, protein recovery, operating flow-rate, chemical stability, and spacer arm and base-matrix chemistry.

During purification process development for biopharmaceuticals significant attention is paid to resin screening and selection by means of extensive empirical studies dealing mainly with selectivity, capacity and flow characteristics. Usually, not much attention is given to the possibility of transient pH changes at the resin screening stage. Nevertheless, such phenomena can have significant implications for the development of a scaleable and robust manufacturing process.

Perhaps, the most widely used chromatographic tool for preparative applications is ion exchange chromatography. pH of the mobile phase is a very important variable in ion exchange chromatography. In some cases, deliberate pH transitions have been exploited to develop more efficient purification processes. Retained pH gradients generated by either polyampholyte or simpler buffer systems have been utilized for chromatofocussing proteins into narrow bands. The ability of these pH gradients to separate protein mixtures has also been investigated.

Unintentional pH changes have also been reported in the literature. Under certain conditions, considerable pH excursions can occur in ion exchange systems even if the pH of the solution entering the column is the same as that with which the column was equilibrated. An increase in pH was observed on an SP Sephadex C-25 column when a column eluted with 1M ammonium acetate, pH 6.8 was re-equilibrated with the starting buffer (10 mM ammonium acetate, pH 6.8) (Karlsson et al., Ion-exchange chromatography. In *Protein Purification: Principles, High-resolution methods and applications*, Janson, J. C. and Ryden, L. (Eds.), Wiley-VCH, New York, 1998, pp 145–205). At the breakthrough of the 10 mM buffer, pH of the effluent was 7.5 and then it had gradually dropped to 6.8. A similar increase in pH (~0.2 units) was reported by the same authors on a weak anion exchange column TSK-DEAE when a 10 mM phosphate buffer, pH 7.6 was replaced with 10 mM phosphate+1M sodium chloride at the same pH.

Helfferich and co-workers have made a detailed analysis of the pH behavior of buffer solutions in ion exchange columns using the wave theory of multicomponent equilibrium (Helfferich and Bennett, 1984, *Reactive Polymers*, 3:51–66). These phenomena have been explained on the basis of local ion exchange and dissociation phenomena between the charged ion exchanger and buffering species in solution. The three-component exchange of chloride, acetate and hydroxide ions has been used to predict some of these phenomena in anion exchange resins (Helfferich and Bennett, 1984, *Solvent Extraction and Ion Exchange*, 2(7&8):1151–184). Jansen et al. have modeled these phenomena by a complex model involving a thermodynamic model of equilibrium on ion exchange, Donnan potential and reaction equilibria to get more accurate predictions (Jansen et al., 1996, *AIChE Journal*, 42(7):1925–1937).

However, most of the observations in the literature have been made with dilute buffers at pHs at which they buffer weakly, hence the observations were not entirely unexpected. These studies did not investigate transient pH change phenomena using ion exchange media widely employed in the biotechnology industry or using buffers that buffer strongly at the pH of the experiments. Additionally, the contribution of the stationary phase backbone to these equilibria and their effect on transient pH phenomena was not been investigated. Accordingly, the direct impacts of these phenomena on process chromatography as practiced in the biopharmaceutical arena have not been clearly elucidated.

The present invention concerns the elucidation of the potential mechanisms behind such transient pH changes during chromatography processes, and provides practical methods to control their occurrence.

SUMMARY OF THE INVENTION

The invention relates to methods of preventing or minimizing unexpected transient pH transitions that can occur during chromatography. In particular, the invention provides methods of chromatographing proteins on a solid phase under selected conditions with a buffer, preferably a buffer having a broad pKa range, thereby controlling pH transitions during elution. In further embodiments, the invention also includes equilibrating the solid phase with the buffer prior to applying the protein to the solid phase. The solid phase can have a solid phase backbone that can be charged. A example of such solid phase backbones is polymethacrylate backbones.

The method is particularly useful for purifying proteins or protein preparations that are sensitive to pH changes. An example of such a protein is a soluble form of the IL-1 receptor type II protein. Thus, in one aspect, the invention provides a method comprising equilibrating a cation exchange solid phase with a first buffer having a broad pKa range, applying an IL-1 receptor type II protein to the solid phase in the first buffer, and eluting the protein from the solid phase with a second buffer having a broad pKa range, wherein the buffering species in the second buffer is at a higher concentration than the first buffer, thereby ameliorating a pH drop during elution. In one particular aspect of the invention, the method comprises equilibrating a cation exchange solid phase with 25 mM sodium citrate, applying a solution containing a soluble form of the IL-1 receptor type II protein to the solid phase in the same buffer; and eluting the protein from the solid phase with 100 mM sodium citrate at a pH ranging from about 5.5 to about 8.

Figure 1:
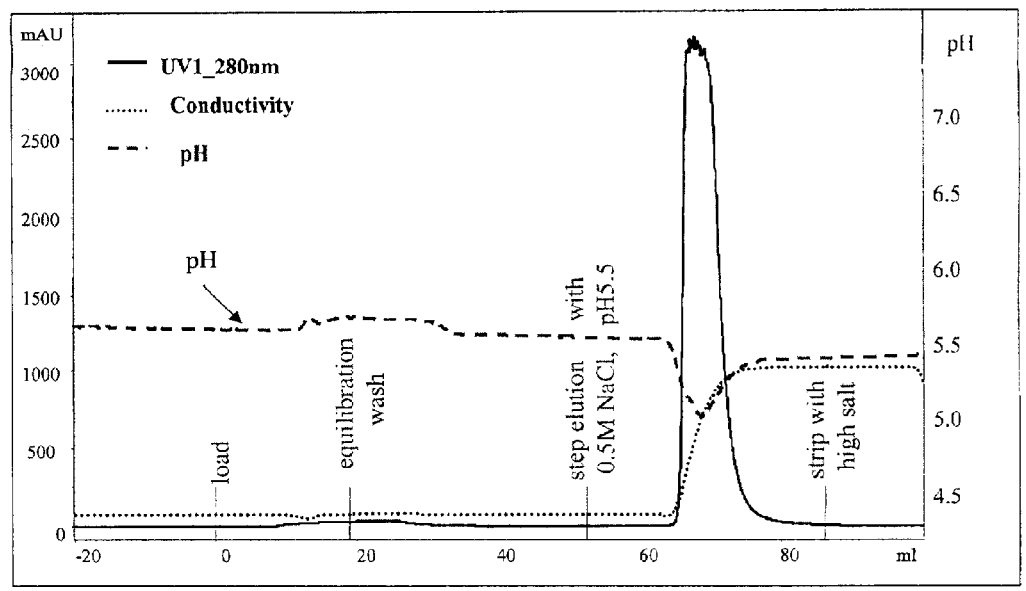
FIG. 1. Elution profile (Absorbance Units—solid line, and pH—dotted line) from Fractogel EMD $SO_3$— column equilibrated in 25 mM citrate buffer, pH 5.5, loaded with 15 mg protein per ml of resin, and eluted with 0.5 M NaCl in 25 mM citrate, pH 5.5.

DETAILED DESCRIPTION OF THE INVENTION pH transitions can be an important factor when developing any chromatography step for purification of proteins. The invention is based, in part, on the recognition that ionization of the solid phase backbone of a chromatography resin can cause significant pH fluctuations during purification processes, and can therefore affect product quality.

Specifically, many preferred ion exchange resins that have functional groups located on linear polymeric chains bound to the matrix by graft polymerization that allow maximum accessibility of the protein to the functional group, thereby resulting in efficient protein purification. Since such resins have relatively long attachment "tentacles" for the functional groups, it was expected that selectivity for the protein would not be affected by the resin backbone chemistry as the protein would not directly interact (non-covalently) with the resin backbone.

However, as described more fully below, it was found that with some resin backbones, small ions can easily penetrate the resin backbone and cause transient pH changes during purification processes. Thus, a problem associated with preparative chromatography has been identified herein. In particular, it has been observed that transient pH changes can occur during chromatography even if the pH of the inlet solution is not changed. This occurred when a column that was equilibrated with a buffer receives another solution in the same buffer and same pH, but at a different salt concentration. Accordingly, such transient pH changes are temporary changes in pH when one switches column inlet from one concentration to another, without changing the pH. The invention is directed at minimizing this effect by careful manipulation of loading and elution conditions during chromatography. Using the methods of the invention, one can ameliorate such pH changes during elution of the protein being purified. By "ameliorating a pH change during elution" is meant that the pH of the eluate does not vary from the pH of the loading inlet by more than about 0.2 pH units. The pH change can be a drop in pH (e.g., in the case of cation exchange chromatography) or a rise in pH (e.g., in the case of anion exchange chromatography).

Accordingly, in one aspect, the invention entails eluting proteins during chromatography with a buffer having a broad pKa range, thereby controlling pH transitions during elution. The invention also includes equilibrating the solid phase with the buffer having a broad pKa range prior to applying the protein to the solid phase. The "solid phase" is understood in the art of chromatography to be the chromatography material or resin; the solid phase can be maintained in any form useful for separation of proteins such as in a column form or in a batch process. By "solid phase backbone" is meant the backbone, plus the linker arm, plus the tentacles (if any) of the solid phase, but excluding the charged functional groups.

The invention finds particular use when the solid phase backbone can be charged, e.g., protonated, at the working pH. By moieties that can be "charged" is meant any chemical moiety bearing an atom that possesses a charge at a particular pH. These moieties could be deliberately placed as a functional group as in ion exchange or be accidental (on the solid phase backbone) as noted herein. For example, carboxylic acid groups on the solid phase backbone can be protonated. Accordingly, a popular solid phase backbone that can be charged is polymethacrylate. Polystyrene groups can also be charged. One can test for the ability of a solid phase backbone to be charged by looking at different materials with the same functional group, but different solid phase backbones, as described below by way of an illustrative example.

By "ion exchange chromatography" is meant chromatography techniques that rely predominately upon charge to separate components in a mixture. Ion exchange chromatography can be cationic, where the solid phase is negatively charged, or anionic, where the solid phase is positively charged. However, the methods of the invention can be used in any chromatography method where a solid phase backbone that can be charged (e.g., protonated) is subjected to a change in salt concentration during elution conditions. Polymethacrylate backbones can be charged and are employed in a number of different chromatography techniques such as affinity chromatography, where a higher salt buffer is recommended as part of the elution condition.

A buffer having a broad pKa range is a buffer that can control pH over a large number of pH units, preferably over at least 1 pH unit, more preferably over at least 3 pH units. Examples of such buffers are citrate buffer (with pKa's of 3.13, 4.76 and 6.4), phosphate buffer (with pKa's of 2.15, 7.2 and 12.33), and succinate buffer (pKa 3, 4.21, 5.64). Generally, buffers that have pKa's in the range of around 4.5 to around 7 can be used. Still other buffers can be used, even if they do not have a broad pKa range, are malate, pyridine, cacodylate, dimethylglutarate, bis-Tris, Trimethylamine-acetate, and collidine-acetate. Acetate (pKa 4.75), MES (pKa 6.1) and carbonate (pKa 6.35) buffers may be useful, particularly at high buffer concentrations (greater than 0.2 M). Combinations of such buffering species can also be used to as to have a buffer that can control pH over a broad pH range. Buffers are used at the concentrations needed to effectively buffer and/or elute.

Further, the invention may entail eluting the protein from the solid phase using a salt with a low ionizing strength. NaCl has a very high ionizing strength, thus in some aspects of the invention, NaCl is not used alone as the eluting salt without a consequent high concentration (e.g., 100 mM or higher) of a buffer included at the same time. Salts that can be used include but are not limited to fluoride, citrate, acetate, malate, succinate, pyridine, phosphate salts (all forms, e.g., Na, K, NH4, Li, Mg, Ca, etc.), sulfate salts (all forms), and heparin salts. Indeed, any compound with a carboxylic acid group, any compound with a sulfonic acid group, any compound with a phosphoric acid group, any alkaline metal salts, and any alkaline earth metal salts can be used. More preferred salts can be sodium citrate, succinate, sulfate, formate, malate, trimethylamine and/or puridine. Most preferred salts are those that also function as buffers such as, for example, sodium citrate. The salt is added in an amount sufficient to elute the protein from the solid phase.

The invention can be used to purify just about any protein, and is particularly advantageous for proteins that are pH sensitive (either high pH or lo pH) or preparations of proteins that are subject to degradation at low pH (e.g., due to proteases). A protein is generally understood to be a polypeptide of at least about 10 amino acids, more preferably at least about 25 amino acids, even more preferably at least about 75 amino acids, and most preferably at least about 100 amino acids.

Generally, the methods of the invention are useful for purifying recombinant proteins. Recombinant proteins are proteins produced by the process of genetic engineering. The term "genetic engineering" refers to any recombinant DNA or RNA method used to create a host cell that expresses a gene at elevated levels, at lowered levels, or a mutant form of the gene. In other words, the cell has been transfected, transformed or transduced with a recombinant polynucleotide molecule, and thereby altered so as to cause the cell to alter expression of a desired protein. Methods and vectors for genetically engineering cells and/or cell lines to express a protein of interest are well known to those skilled in the art; for example, various techniques are illustrated in *Current Protocols in Molecular Biology*, Ausubel et al., eds. (Wiley & Sons, New York, 1988, and quarterly updates) and Sambrook et al., *Molecular Cloning: A Laboratory Manual* (Cold Spring Laboratory Press, 1989). Genetic engineering techniques include but are not limited to expression vectors, targeted homologous recombination and gene activation (see, for example, U.S. Pat. No. 5,272,071 to Chappel) and trans activation by engineered transcription factors (see, for example, Segal et al., 1999, Proc. Natl. Acad. Sci. USA 96(6):2758–63).

The proteins can be produced recombinantly in either prokaryotic or eukaryotic cells. The proteins can be derived from genetically engineered plants, transgenic animals, or can be secreted by production cells adapted to grow in cell culture. Production cells can be bacterial (e.g., *E. coli, Streptomyces* spp., and *Bacillus* spp.), fungal (e.g., *Aspergillus*), invertebrate-derived (e.g., insect) or mammalian. Examples of mammalian cells commonly used in the industry are CHO, VERO, BHK, HeLa, CV1 (including Cos), MDCK, 293, 3T3, myeloma cell lines (especially murine), PC12 and WI38 cells. Particularly preferred host cells are Chinese hamster ovary (CHO) cells, which are widely used for the production of several complex recombinant proteins, e.g. cytokines, clotting factors, and antibodies (Brasel et al., 1996, Blood 88:2004–2012; Kaufman et al., 1988, J.Biol Chem 263: 6352–6362; McKinnon et al., 1991, J Mol Endocrinol 6:231–239; Wood et al., 1990, J. Immunol 145:3011–3016). The dihydrofolate reductase (DHFR)-deficient mutant cell line (Urlaub et al., 1980, Proc Natl Acad Sci USA 77:4216–4220), DXB11 and DG-44, are the CHO host cell lines of choice because the efficient DHFR selectable and amplifiable gene expression system allows high level recombinant protein expression in these cells (Kaufman R. J., 1990, Meth Enzymol 185:527–566). In addition, these cells are easy to manipulate as adherent or suspension cultures and exhibit relatively good genetic stability. CHO cells and recombinant proteins expressed in them have been extensively characterized and have been approved for use in clinical manufacturing by regulatory agencies. The polypeptide can also be expressed as a product of transgenic animals, e.g., as a component of the milk of transgenic cows, goats, pigs, or sheep which are characterized by somatic or germ cells containing a nucleotide sequence encoding the polypeptide.

Particularly preferred proteins are protein-based drugs, also known as biologics. Preferably, the proteins are expressed as extracellular products. Proteins that can be purified using the methods of the invention include but are not limited to a Flt3 ligand, a CD40 ligand, erythropoeitin, thrombopoeitin, calcitonin, Fas ligand, ligand for receptor activator of NF-kappa B (RANKL), TNF-related apoptosis-inducing ligand (TRAIL), ORK/Tek, thymic stroma-derived lymphopoietin, granulocyte colony stimulating factor, granulocyte-macrophage colony stimulating factor, mast cell growth factor, stem cell growth factor, epidermal growth factor, RANTES, growth hormone, insulin, insulinotropin, insulin-like growth factors, parathyroid hormone, interferons, nerve growth factors, glucagon, interleukins 1 through 18, colony stimulating factors, lymphotoxin-β, tumor necrosis factor, leukemia inhibitory factor, oncostatin-M, and various ligands for cell surface molecules Elk and Hek (such as the ligands for eph-related kinases, or LERKS). Descriptions of proteins that can be purified according to the inventive methods may be found in, for example, *Human Cytokines: Handbook for Basic and Clinical Research, Vol. II* (Aggarwal and Gutterman, eds. Blackwell Sciences, Cambridge Mass., 1998); *Growth Factors:A Practical Approach* (McKay and Leigh, eds., Oxford University Press Inc., New York, 1993) and *The Cytokine Handbook* (A W Thompson, ed.; Academic Press, San Diego Calif.; 1991).

Purification of the receptors for any of the aforementioned proteins can also be improved using the inventive methods, including the receptors for both forms of tumor necrosis factor receptor (referred to as p55 and p75), Interleukin-1 receptors (type 1 and 2), Interleukin-4 receptor, Interleukin-15 receptor, Interleukin-17 receptor, Interleukin-18 receptor, granulocyte-macrophage colony stimulating factor receptor, granulocyte colony stimulating factor receptor, receptors for oncostatin-M and leukemia inhibitory factor, receptor activator of NF-kappa B (RANK), receptors for TRAIL, and receptors that comprise death domains, such as Fas or Apoptosis-Inducing Receptor (AIR). A particularly preferred receptor is a soluble form of the IL-1 receptor type II; such proteins are described in U.S. Pat. No. 5,767,064, incorporated herein by reference in its entirety.

Other proteins that can be purified using the inventive methods include cluster of differentiation antigens (referred to as CD proteins), for example, those disclosed in *Leukocyte Typing VI (Proceedings of the VIth International Workshop and Conference*; Kishimoto, Kikutani et al., eds.; Kobe, Japan, 1996), or CD molecules disclosed in subsequent workshops. Examples of such molecules include CD27, CD30, CD39, CD40; and ligands thereto (CD27 ligand, CD30 ligand and CD40 ligand). Several of these are members of the TNF receptor family, which also includes 41BB and OX40; the ligands are often members of the TNF family (as are 41BB ligand and OX40 ligand); accordingly, members of the TNF and TNFR families can also be purified using the present invention.

Proteins that are enzymatically active can also be purified according to the instant invention. Examples include metalloproteinase-disintegrin family members, various kinases, glucocerebrosidase, superoxide dismutase, tissue plasminogen activator, Factor VIII, Factor IX, apolipoprotein E, apolipoprotein A-I, globins, an IL-2 antagonist, alpha-1 antitrypsin, TNF-alpha Converting Enzyme, and numerous other enzymes. Ligands for enzymatically active proteins can also be purified by applying the instant invention.

The inventive compositions and methods are also useful for purification of other types of recombinant proteins, including immunoglobulin molecules or portions thereof, and chimeric antibodies (i.e., an antibody having a human constant region couples to a murine antigen binding region) or fragments thereof. Numerous techniques are known by which DNA encoding immunoglobulin molecules can be manipulated to yield DNAs capable of encoding recombinant proteins such as single chain antibodies, antibodies with enhanced affinity, or other antibody-based polypeptides (see, for example, Larrick et al., 1989, Biotechnology 7:934–938; Reichmann et al., 1988, Nature 332:323–327; Roberts et al., 1987, Nature 328:731–734; Verhoeyen et al., 1988, Science 239:1534–1536; Chaudhary et al., 1989, Nature 339:394–397). Preparations of fully human antibodies (such as are prepared using transgenic animals, and optionally further modified in vitro), as well as humanized antibodies, can also be used in the invention. The term humanized antibody also encompasses single chain antibodies. See, e.g., Cabilly et al., U.S. Pat. No. 4,816,567; Cabilly et al., European Patent No. 0,125,023 B1; Boss et al., U.S. Pat. No. 4,816,397; Boss et al., European Patent No. 0,120,694 B1; Neuberger, M. S. et al., WO 86/01533; Neuberger, M. S. et al., European Patent No. 0,194,276 B1; Winter, U.S. Pat. No. 5,225,539; Winter, European Pat. No. 0,239,400 B 1; Queen et al., European Pat. No. 0 451 216 B1; and Padlan, E. A. et al., EP 0 519 596 A1.

Various fusion proteins can also be purified using the inventive methods. Examples of such fusion proteins include proteins expressed as a fusion with a portion of an immunoglobulin molecule, proteins expressed as fusion proteins with a zipper moiety, and novel polyfunctional proteins such as a fusion proteins of a cytokine and a growth factor (i.e., GM-CSF and IL-3, MGF and IL-3). WO 93/08207 and WO 96/40918 describe the preparation of various soluble oligomeric forms of a molecule referred to as CD40L, including an immunoglobulin fusion protein and a zipper fusion protein, respectively; the techniques discussed therein are applicable to other proteins. Any of the above molecules can be expressed as a fusion protein including but not limited to the extracellular domain of a cellular receptor molecule, an enzyme, a hormone, a cytokine, a portion of an immunoglobulin molecule, a zipper domain, and a epitope.

The protein can be a from a cell culture supernatant, cell extract, or a partially purified fraction from the same. By "partially purified" means that some fractionation procedure, or procedures, have been carried out, but that more polypeptide species (at least 10%) than the desired protein is present. By the term "isolating" is meant physical separation of at least one component in a mixture away from other components in a mixture. Isolating components or particular conformations of a protein can be achieved using any purification method that tends to separate such components.

The preparation of recombinant protein can be prepared initially by culturing recombinant host cells under culture conditions suitable to express the polypeptide. The resulting expressed polypeptide can then be purified, or partially purified, from such culture or component (e.g., from culture medium or cell extracts or bodily fluid) using known processes. Fractionation procedures can include but are not limited to one or more steps of filtration (e.g., tangential flow filtration), centrifugation, precipitation, phase separation, affinity purification, gel filtration, ion exchange chromatography (cation exchange and/or anion exchange exchange), hydrophobic interaction chromatography (HIC; using such resins as phenyl ether, butyl ether, or propyl ether), hydroxyapatite chromatography, HPLC, electrophoretic techniques (e.g., electrophoresis, electroelution, isoelectric focusing), phase separation (e.g., PEG-dextran phase separation), or some combination of above.

For example, the purification of the polypeptide can include an affinity column containing agents which will bind to the polypeptide; one or more column steps over such affinity resins as concanavalin A-agarose, heparin-toyopearl® or Cibacrom blue 3GA Sepharose®; one or more steps involving elution; and/or immunoaffinity chromatography. The polypeptide can be expressed in a form that facilitates purification. For example, it may be expressed as a fusion polypeptide, such as those of maltose binding polypeptide (MBP), glutathione-S-transferase (GST) or thioredoxin (TRX). Kits for expression and purification of such fusion polypeptides are commercially available from New England BioLab (Beverly, Mass.), Pharmacia (Piscataway, N.J.) and InVitrogen, respectively. The polypeptide can be tagged with an epitope and subsequently purified by using a specific antibody directed to such epitope. One such epitope (FLAG®) is commercially available from Kodak (New Haven, Conn.). It is also possible to utilize an affinity column comprising a polypeptide-binding polypeptide, such as a monoclonal antibody to the recombinant protein, to affinity-purify expressed polypeptides. Other types of affinity purification steps can be a Protein A or a Protein G column, which affinity agents bind to proteins that contain Fc domains. Polypeptides can be removed from an affinity column using conventional techniques, e.g., in a high salt elution buffer and then dialyzed into a lower salt buffer for use or by changing pH or other components depending on the affinity matrix utilized, or can be competitively removed using the naturally occurring substrate of the affinity moiety.

Some or all of the foregoing purification steps, in various combinations, can also be employed to prepare an appropriate preparation of a protein in conjunction with the methods of the invention, and/or to further purify the protein. The polypeptide that is substantially free of other polypeptides is defined as an "isolated polypeptide".

The polypeptide can also be produced by known conventional chemical synthesis. Methods for constructing polypeptides by synthetic means are known to those skilled in the art. The synthetically-constructed polypeptide sequences can be glycosylated in vitro.

The desired degree of final purity depends on the intended use of the polypeptide. A relatively high degree of purity is desired when the polypeptide is to be administered in vivo, for example. In such a case, the polypeptides are purified such that no polypeptide bands corresponding to other polypeptides are detectable upon analysis by SDS-polyacrylamide gel electrophoresis (SDS-PAGE). It will be recognized by one skilled in the pertinent field that multiple bands corresponding to the polypeptide can be visualized by SDS-PAGE, due to differential glycosylation, differential post-translational processing, and the like. Most preferably, the polypeptide of the invention is purified to substantial homogeneity, as indicated by a single polypeptide band upon analysis by SDS-PAGE. The polypeptide band can be visualized by silver staining, Coomassie blue staining, or (if the polypeptide is radiolabeled) by autoradiography.

The invention also optionally encompasses further formulating the proteins. By the term "formulating" is meant that the proteins can be buffer exchanged, sterilized, bulk-packaged and/or packaged for a final user. For purposes of the invention, the term "sterile bulk form" means that a formulation is free, or essentially free, of microbial contamination (to such an extent as is acceptable for food and/or drug purposes), and is of defined composition and concentration. The term "sterile unit dose form" means a form that is appropriate for the customer and/or patient administration or consumption. Such compositions can comprise an effective amount of the protein, in combination with other components such as a physiologically acceptable diluent, carrier, or excipient. The term "pharmaceutically acceptable" means a non-toxic material that does not interfere with the effectiveness of the biological activity of the active ingredient(s).

Formulations suitable for administration include aqueous and non-aqueous sterile injection solutions which may contain anti-oxidants, buffers, bacteriostats and solutes which render the formulation isotonic with the blood of the recipient; and aqueous and non-aqueous sterile suspensions which may include suspending agents or thickening agents. The polypeptides can be formulated according to known methods used to prepare pharmaceutically useful compositions. They can be combined in admixture, either as the sole active material or with other known active materials suitable for a given indication, with pharmaceutically acceptable diluents (e.g., saline, Tris-HCl, acetate, and phosphate buffered solutions), preservatives (e.g., thimerosal, benzyl alcohol, parabens), emulsifiers, solubilizers, adjuvants and/or carriers. Suitable formulations for pharmaceutical compositions include those described in *Remington's Pharmaceutical Sciences*, 16th ed. 1980, Mack Publishing Company, Easton, Pa. In addition, such compositions can be complexed with polyethylene glycol (PEG), metal ions, or incorporated into polymeric compounds such as polyacetic acid, polyglycolic acid, hydrogels, dextran, etc., or incorporated into liposomes, microemulsions, micelles, unilamellar or multi-lamellar vesicles, erythrocyte ghosts or spheroblasts. Suitable lipids for liposomal formulation include, without limitation, monoglycerides, diglycerides, sulfatides, lysolecithin, phospholipids, saponin, bile acids, and the like. Preparation of such liposomal formulations is within the level of skill in the art, as disclosed, for example, in U.S. Pat. No. 4,235,871; U.S. Pat. No. 4,501,728; U.S. Pat. No. 4,837,028; and U.S. Pat. No. 4,737,323. Such compositions will influence the physical state, solubility, stability, rate of in vivo release, and rate of in vivo clearance, and are thus chosen according to the intended application, so that the characteristics of the carrier will depend on the selected route of administration. Sustained-release forms suitable for use include, but are not limited to, polypeptides that are encapsulated in a slowly-dissolving biocompatible polymer (such as the alginate microparticles described in U.S. Pat. No. 6,036,978), admixed with such a polymer (including topically applied hydrogels), and or encased in a biocompatible semi-permeable implant.

The invention having been described, the following examples are offered by way of illustration, and not limitation.

EXAMPLE pH Changes During Sample Elution

In this experiment, pH was monitored during a typical cation exchange purification step of recombinant protein. The protein that was purified was a soluble form of the IL-1 receptor type II protein, which has been shown to be sensitive to low pH (pH 5 and below).

A 1×12 cm Fractogel EMD $SO_3$— column (Merck KGaA, Darmstadt, Germany) was equilibrated and loaded at 25 mM citrate buffer, pH 5.5. After loading (15 mg protein per ml of resin), the column was washed with the same buffer. Protein was eluted with 0.5 M NaCl in 25 mM citrate, pH 5.5. The column trace, shown in FIG. 1, indicated that as the protein eluted from the column, a dip in pH from about pH 5.6 to below pH 5 was observed. This pH dip was not due to the change in any inlet pH or buffer, but was associated with the change in inlet salt concentration.

Figure 2:
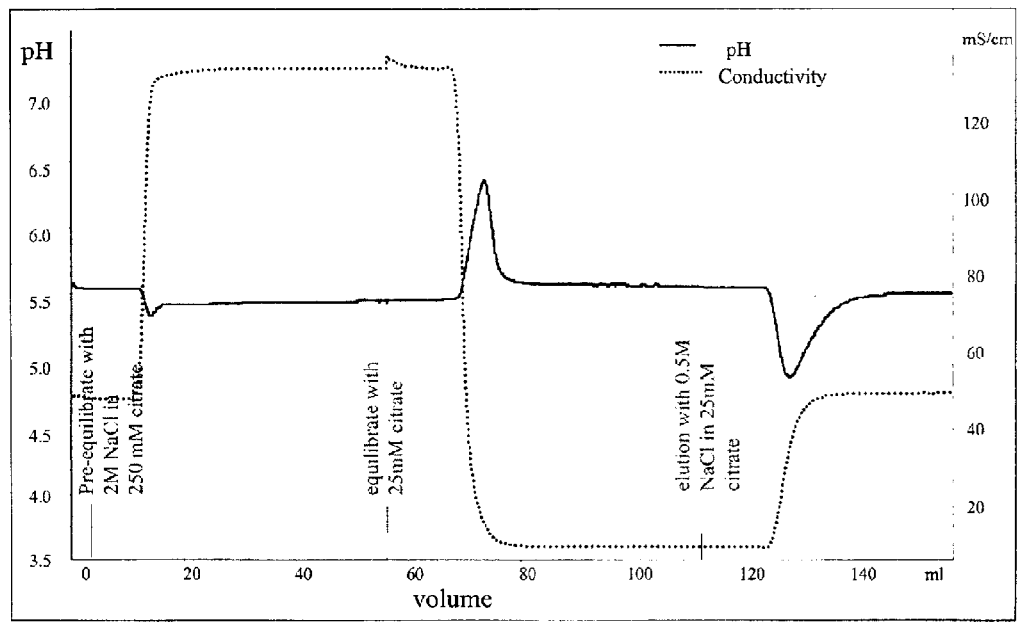
FIG. 2. Elution profile (Absorbance Units—solid line, and pH—dotted line) from Fractogel EMD $SO_3$— column equilibrated in 25 mM citrate buffer, pH 5.5, mock loaded with no protein, and eluted with 0.5 M NaCl in 25 mM citrate, pH 5.5.

In order to determine whether the pH dip was associated with the presence of the protein, a blank column run was performed without any protein. The column, in elution buffer of 0.5 M NaCl in 25 mM citrate, pH 5.5, was equilibrated with 25 mM citrate buffer, pH 5.5. As the column equilibrated, a pH spike occurred, as shown in the column trace in FIG. 2. When a mock elution step was performed, again at 0.5 M NaCl in 25 mM citrate, pH 5.5, a similar pH dip was observed. Thus, these pH flunctuations occurred even in the absence of the protein.

Step changes in the inlet salt concentration in ion exchange chromatography have been observed to result in transient changes in effluent pH. The direction of this transition has been observed to depend on the charge on the stationary phase, with a decrease observed for cation exchange chromatography (and vice versa for anion exchange). These pH changes have been found to occur even when the elution buffer is identical to the equilibration buffer, except for the presence of a high concentration of the eluting salt in the elution buffer. Such pH transitions during elution can become significant in process chromatography when the product is sensitive to pH changes.

EXAMPLE

Effect of Column Pre-equilibration & Equilibration

Figure 3:
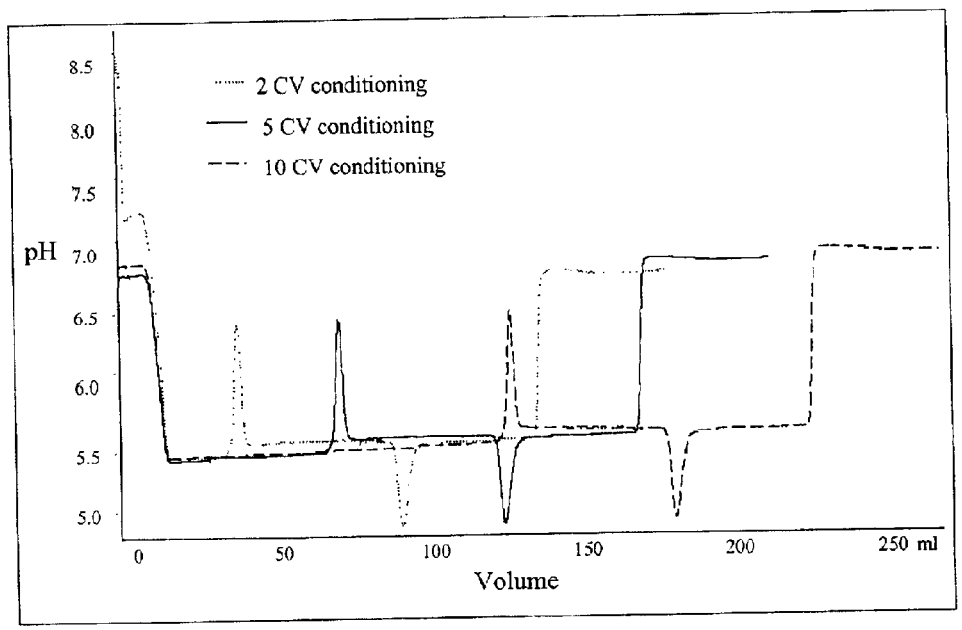
FIG. 3. Stacked chromatogram showing pH traces from the three experiments done with varying pre-equilibration volume.

Incomplete column equilibration has often been associated with transient pH fluctuations in ion exchange chromatography. A pre-equilibration step containing a several fold higher concentration of the buffering salts is often included prior to the equilibration step to ensure that the column is saturated with components of the equilibration buffer. The pre-equilibration step has been observed to reduce the duration and volume of the equilibration step and is often employed in process chromatography. In order to eliminate the possibility of incomplete column equilibration, the column was pre-equilibrated (conditioned) with a solution containing 2M NaCl in 10× concentration of citrate buffer for 2, 5 and 10 column volumes. FIG. 3 shows the stacked pH traces from the three experiments with varying pre-equilibration volumes. As can be seen in the figure, the magnitude of the transient pH decrease was not dependent on the volume of column pre-equilibration. A similar result was obtained when the column was equilibrated for an extended duration (with the equilibration buffer) without a prior conditioning step. Thus, the transient pH phenomena described here are not due to incomplete column equilibration.

EXAMPLE

Effect of Equilibration Buffer Concentration

Figure 4:
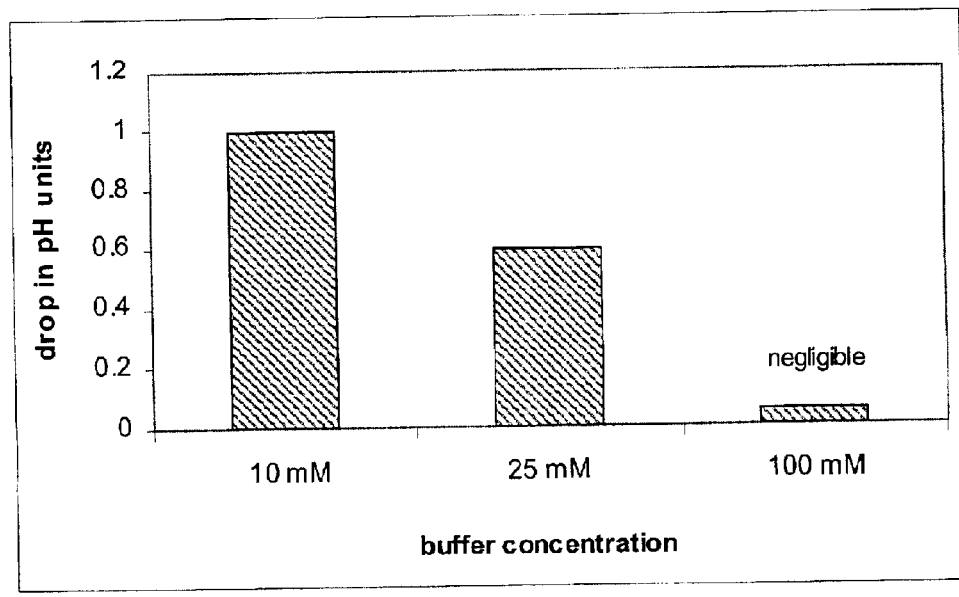
FIG. 4. Variation of the magnitude of pH decrease with varying concentration of citrate buffer FIG. 5. Effect of various buffers and eluting salt on the magnitude of the transient decrease in pH.

The results presented so far have employed a 25 mM citrate base buffer system. FIG. 4 shows the magnitude of pH decrease observed with varying concentrations of the base citrate buffer. Three concentrations of citrate buffer were investigated in this case: 10, 25, and 100 mM. The magnitude of the pH dip decreases with increasing buffer concentration due to an increase in buffering capacity. Increasing the concentration of the buffering species might not be feasible for the purification process due to the possibility of a decrease in protein capacity at higher buffer salt concentrations. However, this shows the importance of buffering capacity of the solution and raises the possibility of employing an alternative buffer that can alleviate this problem.

EXAMPLE

Effect of Buffer and Elution Salts

Figure 5:
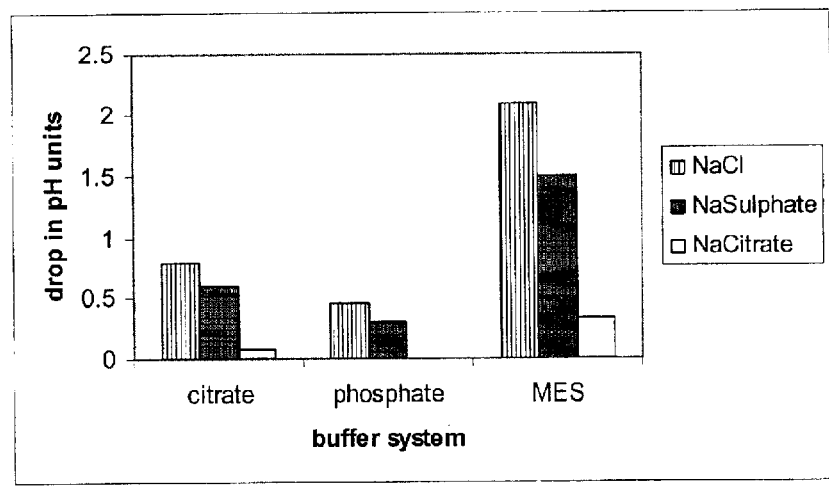

The results presented so far have employed sodium citrate as the buffering species and sodium chloride as the eluting salt. A matrix of experiments was set up with various combinations of buffers and eluting salts. For a cation exchange system, the concentration of the cationic species in the buffer is an important parameter. The buffers used were citrate, phosphate and MES, all at the same concentration of the cation (25 mM $Na^+$) and at the same pH (pH 6.0). The eluting salts used were sodium chloride, sodium sulfate and sodium citrate, all at a concentration that would yield 0.5M $Na^+$ ion concentration based on their molecular formulas. FIG. 5 summarizes the magnitude of the pH dip observed for all of these combinations of buffer and eluting salt. Comparing buffer species, it can be seen that the greatest magnitude of pH dip was observed for MES. The least pH dip occurred with a phosphate buffer while citrate showed an intermediate dip. This order was found to hold true for all three elution salts investigated. Conversely, for any of the buffer systems, the trend for pH dip among the three chosen elution salts was as follows: sodium chloride>sodium sulfate>sodium citrate.

EXAMPLE

Proposed Mechanism for Transient pH Changes

Figure 6:
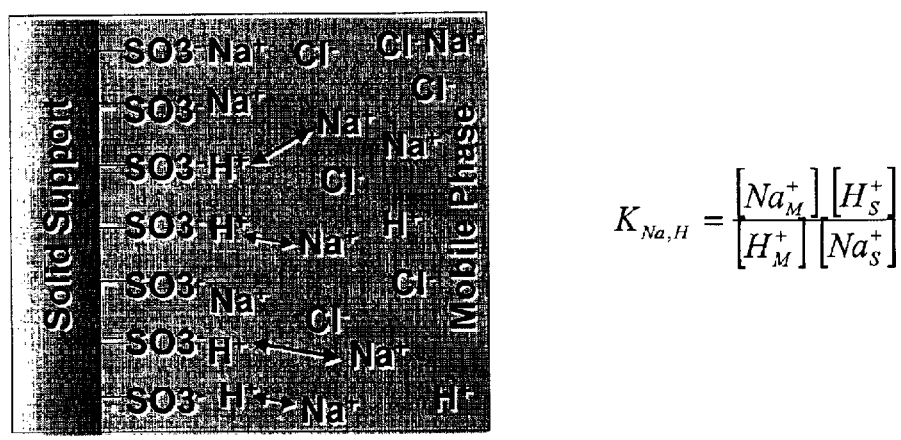
FIG. 6. General schematic for ion exchange equilibrium.

To examine the mechanism for transient pH dips observed on cation exchange, let us consider a cation exchanger in the hydrogen form. When this ion exchanger is brought in contact with a solution containing $Na^+$ ions, equilibrium is established between the sodium and hydrogen ions on the stationary phase with those in the mobile phase. FIG. 6 shows a general schematic for this equilibrium. This ion exchange equilibrium constant ($K_{Na, H}$) has been defined by Helfferich and Bennett, supra, as follows:

$$K_{Na,H} = \frac{[Na_M^+][H_S^+]}{[H_M^+][Na_S^+]}$$

wherein:
$Na_M^+$ concentration of sodium ions in the mobile phase,
$Na_S^+$ concentration of sodium ions in the stationary phase,
$H_M^+$ concentration of hydrogen ions in the mobile phase,
$H_S^+$ concentration of hydrogen ions in the stationary phase, and
$K_{Na, H}$ equilibrium constant of counter-ions $Na^+$ and $H^+$ The ratio of the two cations on the stationary phase (in this case $Na^+$ and $H^+$ ions) will be dependent on the acidity of the ion exchanger group on the stationary phase, the relative positions of the two cations in the affinity sequence, wherein $Tl^+>Ag^+>Cs^+>Rb^+>K^+>NH_4^+>Na^+>H^+>Li^+$, and the concentration of both the cations in the mobile phase.

In this example, Fractogel EMD $SO_3^-$ stationary phase is a strong cation exchanger having a very acidic functional group $SO_3^-$. The ion exchanger is initially in the hydrogen form and the equilibration buffer solution contains both $Na^+$ and $H^+$ ions. When the stationary phase is brought in contact with the equilibration buffer, equilibrium is set up which dictates the relative ratio of $Na^+:H^+$ ions on the stationary phase. In general, for any cationic exchanger, a small fraction of the ionic sites will always be taken up by the $H^+$ ions because of this equilibrium. However, passing a front of high salt solution causes an increase in the mobile phase $Na^+$ ion concentration. Since sodium ions have a higher affinity than hydrogen ions (as noted above), the sodium ions in solution ($Na^+_M$) can drive the equilibrium towards an increase in the sodium ions on the stationary phase ($Na^+_S$). However, in order to maintain electroneutrality of the ion exchanger, this should be accompanied by a decrease in adsorbed $H^+$ ions ($H^+_S$) and thereby an increase in the hydrogen ions in the mobile phase ($H^+_M$). In other words, the increased mobile phase $Na^+$ concentration can displace the residual hydrogen ions from the stationary phase. These $H^+$ ions that are released into the mobile phase can cause a temporary reduction in the column effluent pH. Once equilibrium is re-established the pH returns to normal. The exactly opposite phenomenon can happen when the $Na^+$ concentration is reduced after a high salt buffer wash, as was seen in the above Example.

However, an interesting point to note here is that the $SO_3^-$ functional group is extremely acidic. Consequently, it is to be expected that the equilibrium between $Na^+$ and $H^+$ ions on the stationary phase would be almost completely in favor of $Na^+$ ions. In other words, the fraction of the ionic sites taken up by $H^+$ ions would be almost negligible, such that their subsequent release by an increase in the mobile phase $Na^+$ concentration would not be sufficient to result in the observed 0.5–0.6 unit pH dip. An important question to ask is that from where are these $H^+$ ions being released?

Figure 7:
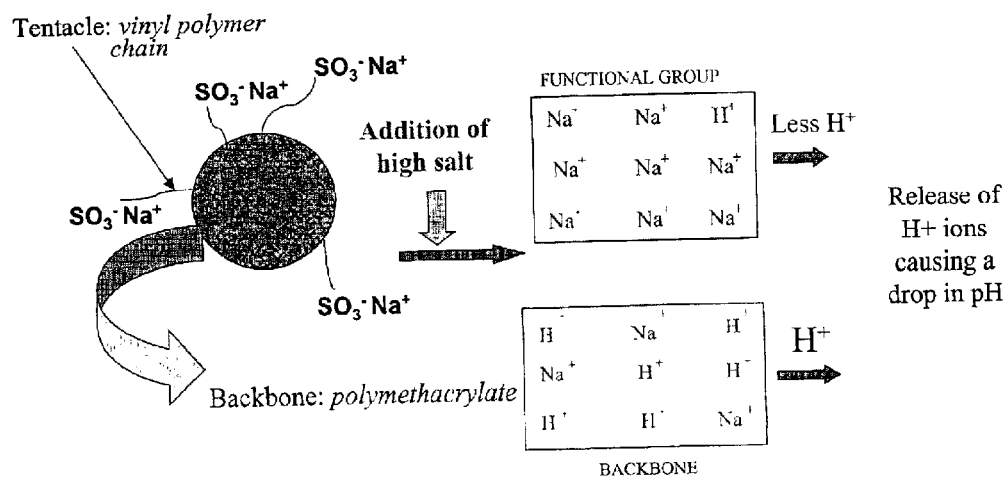
FIG. 7. Schematic of proposed mechanism for pH transition.
Figure 7:
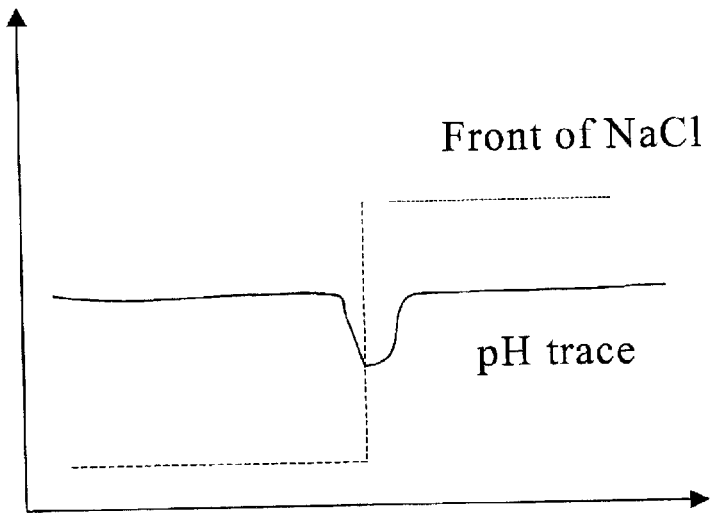

In an attempt to answer this question, the morphology of the Fractogel EMD $SO_3^-$ stationary phase was examined. This stationary phase has a polymethacrylate backbone onto which vinyl polymer chain tentacles containing the functional groups are grafted. The polymethacrylate backbone can contain residual free carboxylic groups that get protonated at acidic pHs. These protonated functional groups can act as secondary cation exchange sites. Since the $COO^-$ functional group is weakly acidic, there would be a significant fraction of ionic sites containing $H^+$ ions under low salt conditions. As explained earlier, under high salt conditions (i.e. under a high concentration of mobile phase $Na^+$ ions), these adsorbed $H^+$ are released causing the pH dip. This mechanism is shown schematically in FIG. 7.

EXAMPLE

Comparison of Different Stationary Phases

Figure 8:
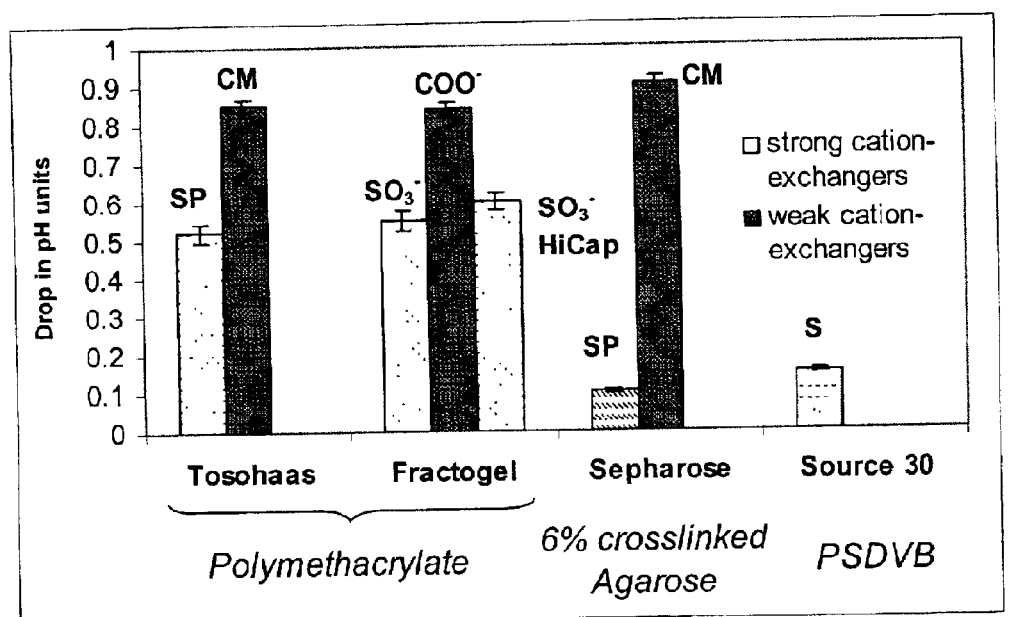
FIG. 8. Comparison of different stationary phases with respect to the magnitude of decrease in pH.

Evidence in favor of the above hypothesis is provided by an examination of transient pH changes on a variety of stationary phases with different resin backbones and functional groups (i.e. strong or weakly acidic). Table 1 lists the stationary phases used for this study, their manufacturing vendors, backbone chemistries and cation exchange functional groups. FIG. 8 summarizes the observed data.

TABLE 1

List of stationary phase with their vendor, backbone and type of functional group

| Stationary phase | Vendor | Backbone chemistry | Particle size μm | Cation exchanger type | Functional group |
|---|---|---|---|---|---|
| Toyopearl SP-650M | Tosohaas | Crosslinked polymethacrylate | 40–90 | strong | $SO_3^-$ |
| Toyopearl CM-650M | Tosohaas | Crosslinked polymethacrylate | 40–90 | weak | $COO^-$ |
| Fractogel EMD $SO3^-$ (M) | EM Industries | Crosslinked polymethacrylate | 40–90 | strong | $SO_3^-$ |
| Fractogel EMD SE HiCap (M) | EM Industries | Crosslinked polymethacrylate | 40–90 | strong | $SO_3^-$ |
| Fractogel EMD $COO^-$ (M) | EM Industries | Crosslinked polymethacrylate | 40–90 | weak | $COO^-$ |
| Sepharose SP | Amersham Pharmacia | 6% cross-linked agarose | 90 | strong | $SO_3^-$ |
| Sepharose CM | Amersham Pharmacia | 6% cross-linked agarose | 90 | weak | $COO^-$ |
| Source 30S | Amersham Pharmacia | Polystyrene divinylbenzene | 30 | strong | $SO_3^-$ |

When comparing strong cation exchangers, both stationary phases with a polymethacrylate backbone (Fractogel and TosoHaas) gave a larger pH dip than the stationary phases with agarose (SP Sepharose) or polystyrene divinyl benzene (PSDVB) backbones (Source S). It must be noted that all of these stationary phases have the same charged functionality ($SO_3^-$ group). Interestingly, the magnitude of pH dip between Tosohaas and Fractogel strong cation exchangers (Tosohaas SP, Fractogel $SO_3^-$ and Fractogel $SO_3^-$ HiCap) are very similar. However, it is to be expected because Fractogel resins are actually Toyopearl resins with tentacles grafted to the core bead. These observations support the hypothesis that protonation of residual carboxylic groups on the polymethacrylate matrix is the major cause for the transient pH changes described here. Additionally, it can be seen from FIG. 8 that among the resins with the same backbone but with different functional groups, weak cation exchangers (TosoHaas CM vs. SP; Fractogel $COO^-$ vs $SO_3^{2-}$) exhibit a greater pH change than the corresponding resin with strong functional groups. This effect is even more pronounced when CM Sepharose is compared to SP Sepharose. In fact, the extent of the pH dip with CM Sepharose is comparable to that for CM TosoHaas and Fractogel $COO^-$. This may relate to the higher density of functional groups on CM Sepharose. The weak cation exchangers have a higher fraction of residual $H^+$ ions bound on their functionality. The subsequent displacement of these $H^+$ ions under high salt conditions causes a transient pH dip in the column effluent.

Thus, this experiment can be used to test a particular solid phase. A solid phase has a solid phase backbone that can be charged when the change in pH of the column effluent from such a solid phase using functional group that is a strong ion exchanger (e.g., $SO_3^-$) is at least 0.2 pH units, more preferably at least 0.3 pH units.

EXAMPLE

Hydrolysis of Fractogel EMD $SO_3^-$ by NaOH

Prolonged exposure of polymethacrylate based stationary phases to very strong alkaline conditions is generally known to cause slow hydrolysis of the methacrylate esters of the matrix copolymer generating a corresponding number of new carboxylic groups. If protonation of carboxylic groups on the methacrylate backbone is responsible for the observed pH dip, generation of new carboxylic groups upon hydrolysis should result in increased pH dips. We examined the observed pH change for the Fractogel EMD $SO_3^-$ stationary phase that was incubated with 1.5(N) NaOH over varying periods of time. It was observed that the magnitude of the pH dip increases with an increase in incubation time with sodium hydroxide. This further strengthens the explanation that charged carboxylic groups on the resin backbone (polymethacrylate in this case) were responsible for observed transient pH changes. It must be noted here that 1.5(N) NaOH is not generally employed in process chromatography. This stationary phase is generally shown to have good base stability under sodium hydroxide concentrations typically used in manufacturing sanitization practice (0.1–0.5N NaOH).

EXAMPLE

Trends with Various Buffering Species

This mechanism can explain the results obtained with various buffering species and eluting salts. In general, buffering capacity for a given buffer is maximum when pH of the solution is equal to its pKa. However, for monoprotic buffering species, the buffering capacity rapidly worsens both above and below the pKa in a bell shaped curve (Stoyanov et al., 1999, *J. Chromatography A*, 838:11–18). As a result, multi-protic buffers can be better buffers for larger pH excursions. This would explain the observation that the magnitude of the pH dip decreased in the order MES (pKa 6.1)>citrate (pKa 3.13, 4.76, 6.4)>phosphate (pKa 2.15, 7.2, 12.33).

Various salts exhibit different degrees of ionization in solution (Hawkes et al, 1996, *J. Chem. Educ.*, 73(5):421–423). The higher the $Na^+$ concentration contributed by the eluting salt, the greater would be the extent of pH dip. Amongst the eluting salts compared in FIG. 5, the degree of ionization is expected to follow the order: sodium chloride>sodium sulfate>sodium citrate (in order of strength of the acid contributing the anion). Consequently, the effective $Na^+$ ion concentration is lower than 0.5 M for both sodium citrate and sodium sulfate. The trend for the pH dip for these salts follows the same trend as their degree of ionization.

EXAMPLE pH Increase on Anion Exchange

Results have also indicated the presence of a pH increase on weak anion exchangers when one moves from a buffer with low salt concentration to a high salt buffer. This observation can be explained by a similar logic to that described above for cation exchange. On anion exchange (with a NaCl salt system), an equilibrium is set up between $OH^-$ ions and $Cl^-$ ions on the stationary and mobile phases. When a buffer containing a high concentration of $Cl^-$ ions is passed through the column, $OH^-$ ions are displaced from the resin surface resulting in a pH increase. This phenomenon has been observed to be prominent only on weak anion exchangers (eg. DEAE functionality), the ratio of $OH^-/Cl^-$ is expected to be strongly in favor of $Cl^-$ ions for strong anion exchange functionalities.

EXAMPLE

Purification of IL-1 Receptor Type II

The above experiments were used to design an ion exchange purification step for a recombinantly expressed soluble form of the human IL-1 receptor type II protein (described in U.S. Pat. No. 5,767,064, incorporated by reference herein).

A 1×12 cm Fractogel EMD SO$_3$— column (Merck KGaA, Darmstadt, Germany) was equilibrated and loaded at 25 mM citrate buffer, pH 5.5. After loading a partially purified preparation of the IL-1 receptor type II protein (15 mg protein per ml of resin), the column was washed with the same buffer.

Elution was conducted with a variety of 100 mM citrate buffers, at pH's ranging from 5.5 to 8. Each of the 100 mM citrate buffers within this pH range worked equally well to elute the protein without a consequent pH dip. 100 mM citrate buffer, pH 8 was chosen as the eluting buffer.

The present invention is not to be limited in scope by the specific embodiments described herein, which are intended as single illustrations of individual aspects of the invention, and functionally equivalent methods and components are within the scope of the invention. Indeed, various modifications of the invention, in addition to those shown and described herein will become apparent to those skilled in the art from the foregoing description and accompanying drawings. Such modifications are intended to fall within the scope of the appended claims.

What is claimed is:

1. A method comprising:
   equilibrating a cation exchange solid phase with a first buffer having a broad pKa range;
   applying an IL-1 receptor type II protein to the solid phase in the first buffer; and
   eluting the protein from the solid phase with a second buffer having a broad pKa range, wherein the buffering species in the second buffer is at a higher concentration than the first buffer, thereby ameliorating a pH drop during elution.

2. The method of claim 1, wherein the first buffer and the second buffer have the same buffering species.

3. The method of claim 1, wherein the concentration of the buffering species in the second buffer is at least twice the concentration of the buffering species in the first buffer.

4. The method of claim 1, wherein the second buffer has a broad pKa range.

5. The method of claim 1, wherein at least one buffering species is selected from the group consisting of sodium citrate and sodium phosphate.

6. The method of claim 1, wherein the solid phase has a solid phase backbone that can be charged.

7. The method of claim 6, wherein the solid phase backbone has a polymethacrylate backbone.

8. The method of claim 2, wherein the buffering species is citrate.

9. The method of claim 8, wherein the first buffer is 25 mM citrate, and the second buffer is 100 mM citrate.

10. The method of claim 8, wherein the pH of the second buffer is from about 5.5 to about 8.

11. The method of claim 1, wherein the pH during the eluting step does not drop below about pH 5.4.

* * * * *